United States Patent
Bihler et al.

(10) Patent No.: US 11,541,244 B2
(45) Date of Patent: Jan. 3, 2023

(54) DETACHABLE SEAL FOR MEDICAL IMPLANTS

(71) Applicant: DYCONEX AG, Bassersdorf (CH)

(72) Inventors: Eckardt Bihler, Uitikon (CH); Marc Hauer, Uster (CH)

(73) Assignee: DYCONEX AG, Bassersdorf (CH)

( * ) Notice: Subject to any disclaimer, the term of this patent is extended or adjusted under 35 U.S.C. 154(b) by 64 days.

(21) Appl. No.: 17/018,575

(22) Filed: Sep. 11, 2020

(65) Prior Publication Data
US 2021/0093871 A1 Apr. 1, 2021

(30) Foreign Application Priority Data
Sep. 27, 2019 (EP) .................................. 19200202

(51) Int. Cl.
*A61N 1/375* (2006.01)
*B29C 65/34* (2006.01)

(52) U.S. Cl.
CPC .......... *A61N 1/3752* (2013.01); *A61N 1/3754* (2013.01); *A61N 1/37512* (2017.08); *A61N 1/3756* (2013.01); *B29C 65/3424* (2013.01)

(58) Field of Classification Search
CPC .............. A61N 1/3752; A61N 1/37512; A61N 1/3754; A61N 1/3756; A61N 1/375; B29C 65/3424
See application file for complete search history.

(56) References Cited

U.S. PATENT DOCUMENTS

| | | | |
|---|---|---|---|
| 6,440,335 B1* | 8/2002 | Kingsbury | G02C 7/02 264/2.2 |
| 2005/0167873 A1* | 8/2005 | Aisenbrey | B29C 70/882 264/113 |
| 2008/0033500 A1* | 2/2008 | Strother | A61N 1/37514 607/36 |
| 2009/0059468 A1* | 3/2009 | Iyer | A61N 1/3754 361/302 |
| 2012/0085750 A1* | 4/2012 | Hauer | H05K 5/066 219/603 |
| 2012/0193125 A1 | 8/2012 | Pavlovic et al. | |
| 2012/0193141 A1 | 8/2012 | Reisinger et al. | |
| 2015/0283374 A1 | 10/2015 | Kronmueller et al. | |
| 2016/0287883 A1* | 10/2016 | Barry | A61N 1/3754 |
| 2017/0056675 A1 | 3/2017 | Bortolin et al. | |
| 2017/0112534 A1* | 4/2017 | Schoonmaker | A61B 5/14532 |
| 2018/0359874 A1* | 12/2018 | Hauer | H01L 24/92 |

* cited by examiner

*Primary Examiner* — Catherine M Voorhees
(74) *Attorney, Agent, or Firm* — Laurence A. Greenberg; Werner H. Stemer; Ralph E. Locher

(57) ABSTRACT

A medical implant includes a first component having a surface and a plurality of electrical contacts and a second component having a surface and a plurality of electrical contacts. Each contact of the first component contacts an assigned contact of the second component in an electrically conducting manner. A seal is disposed between the two surfaces for sealing the contacts. The seal and the two surfaces are formed of a thermoplastic material. The seal is fused to the two surfaces for sealing the contacts and the seal is meltable so as to separate the two components from one another. A method for producing a medical implant is also provided.

15 Claims, 18 Drawing Sheets

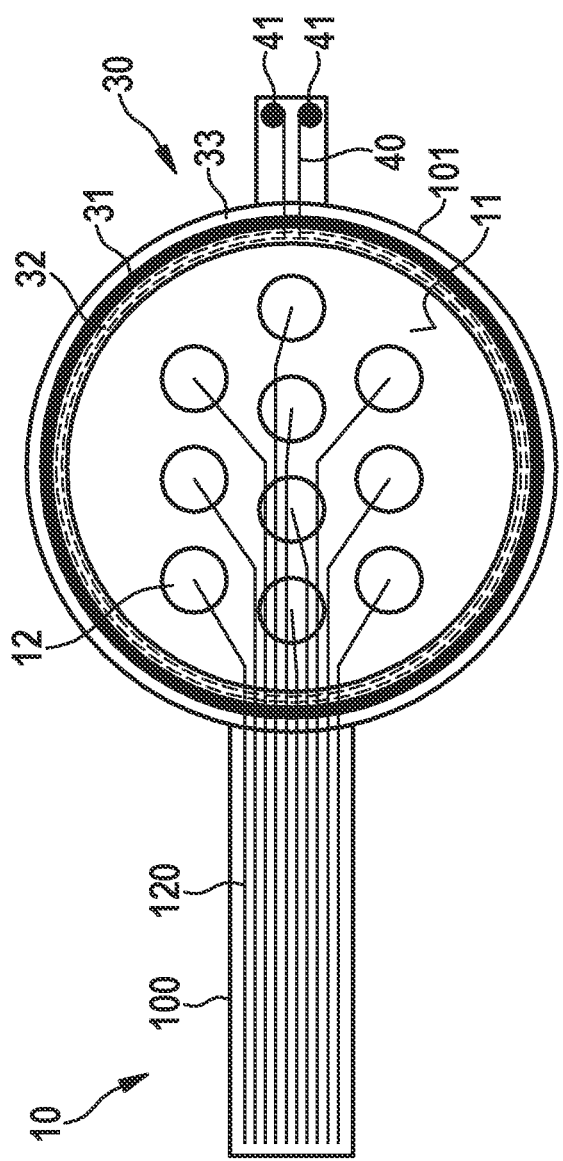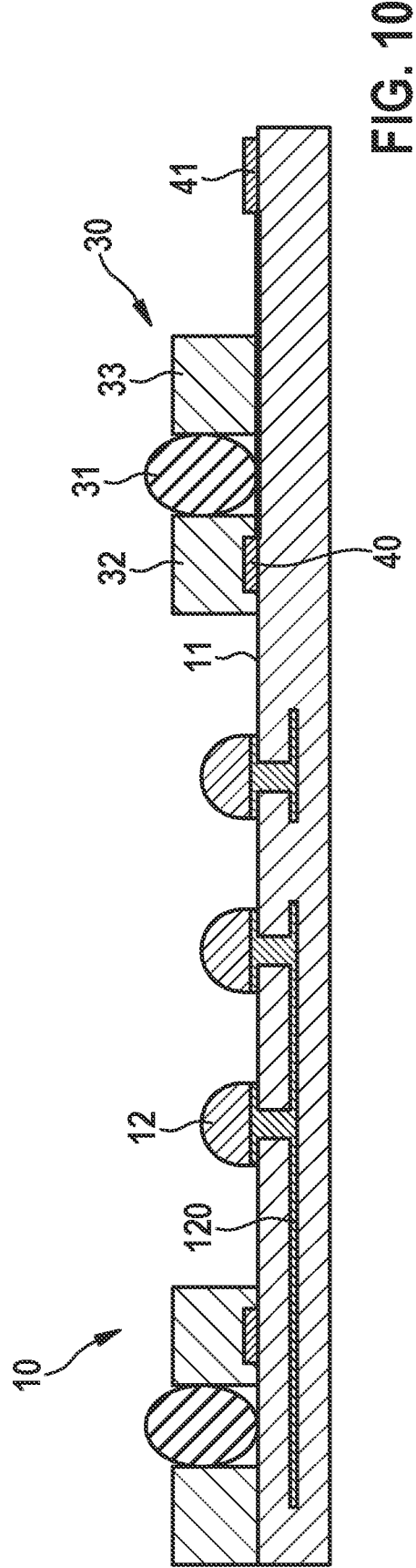

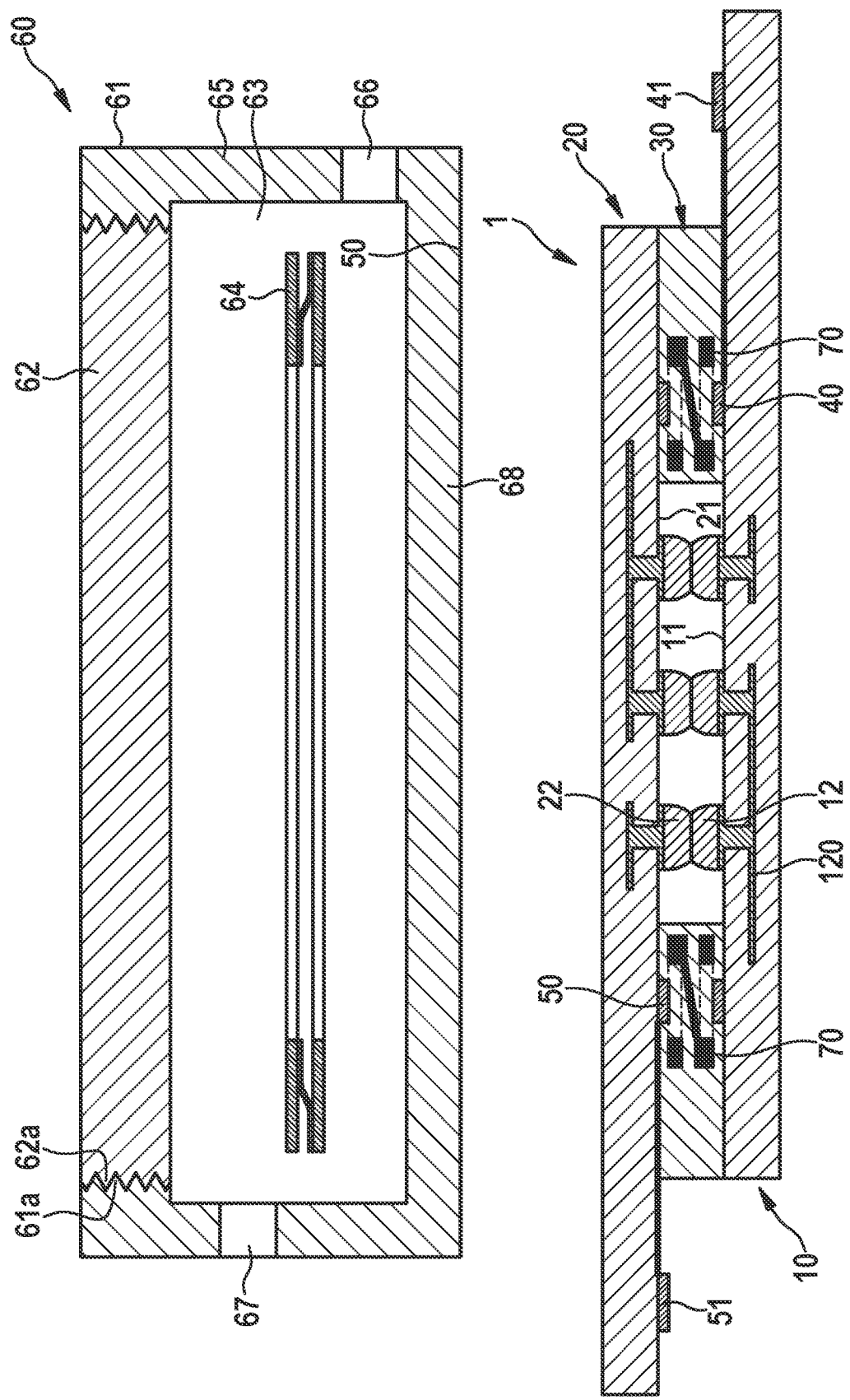

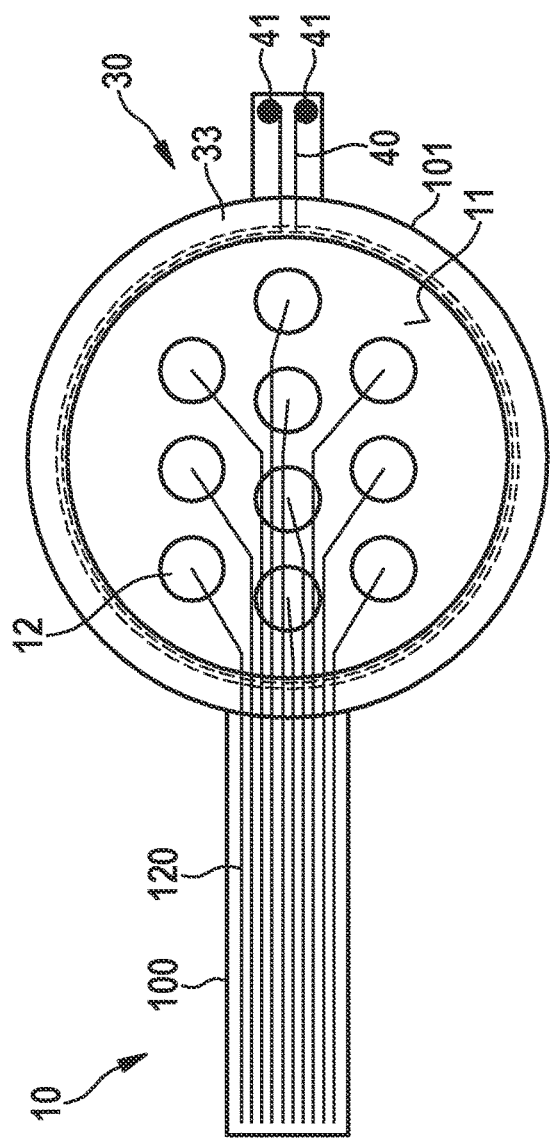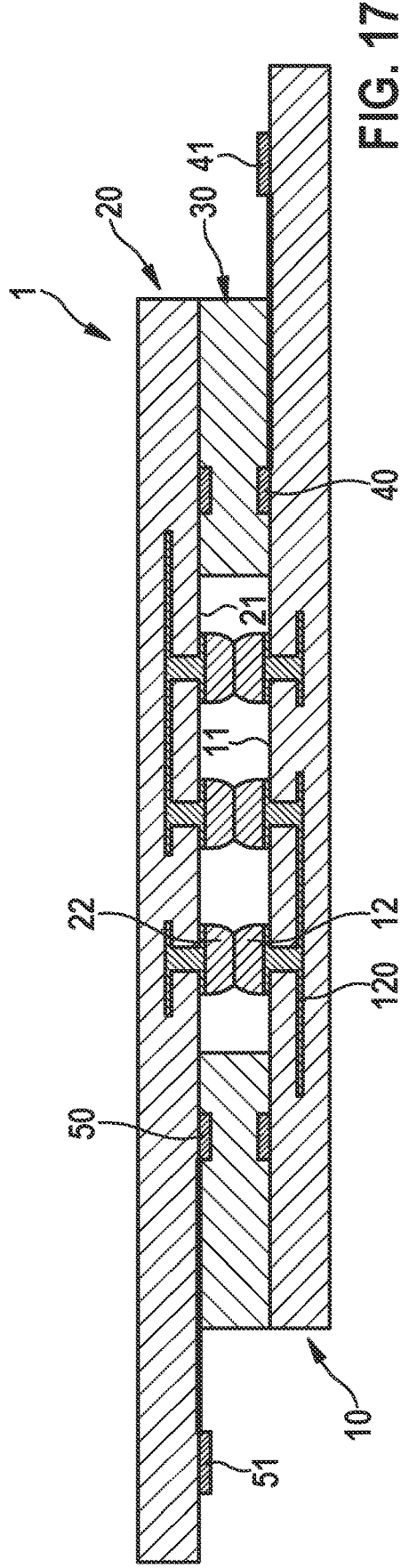

DETACHABLE SEAL FOR MEDICAL IMPLANTS

CROSS-REFERENCE TO RELATED APPLICATION

This application claims the priority, under 35 U.S.C. § 119, of European Patent Application EP 19200202, filed Sep. 27, 2019; the prior application is herewith incorporated by reference in its entirety.

BACKGROUND OF THE INVENTION

Field of the Invention

The present invention relates to a medical implant and a method for producing such an implant.

Seals in medical implants have to provide reliable sealing. With conventional seals made of a rubbery material, sealing is achieved by deformation as a result of an acting force. Certain mechanical requirements have to be met to exert that force. They make the joining system larger and more expensive.

When an already implanted electronic implant is to be removed again, it must be possible to separate the electrode from the implant. Connectors are used for that purpose. Within those connectors, the contact area of the electrode leads has to be sealed from the tissue of the patient.

The systems presently available in the market often use seal plugs that are deformed by using mechanical pressure and thereby exhibit a sealing effect. That increases the complexity of the system and prevents reliable sealing over long periods of time since diffusion along the interfaces cannot be precluded. As a result of that diffusion, each of the contacts in the connector has to be sealed individually.

BRIEF SUMMARY OF THE INVENTION

It is accordingly an object of the invention to provide a medical implant and a method for producing such an implant, which overcome the hereinaforementioned disadvantages and problems of the heretofore-known implants and methods of this general type.

With the foregoing and other objects in view there is provided, in accordance with the invention, a medical implant, comprising:
  a first component, including a surface and a plurality of electrical contacts, the plurality of electrical contacts being in particular disposed on the surface;
  a second component, including a surface and a plurality of electrical contacts, each contact of the first component contacting an assigned contact of the second component in an electrically conducting manner; and
  a seal, which is disposed between the two surfaces for sealing the contacts.

According to the invention, it is provided that the seal and the two surfaces are formed of a thermoplastic material, wherein the seal is melted or fused to the two surfaces for sealing the contacts and is meltable so as to separate the two components from one another.

In other words, the invention thus provides a thermally activatable seal that seals a multi-pin contact area. The seal itself and the interfaces are preferably made of a thermoplastic material.

By introducing heat and applying pressure, the seal melts, mechanically aligns itself, and bonds with the interfaces or surfaces of the components. After the seal has cooled, the pressure can be removed again, and the bond is preserved.

The bond now protects the multi-pin contact area, that is, the contacts of the two components, from environmental conditions. When the contacts or the two components have to be separated again, the seal is heated again, and the two components are separated from one another using a tensile force or compressive force. The contacts of the two components preferably each include a gold metallization. According to one embodiment, it is preferably furthermore provided that each contact of the first component makes mechanical contact with, and thereby contacts, in an electrically conducting manner, the assigned contact of the second component.

The aforementioned meltable seal preferably has an annular or a circumferential configuration and surrounds or extends around the aforementioned contacts.

According to one embodiment of the invention, it is furthermore provided that the thermoplastic material includes or essentially consists of a liquid crystal polymer.

According to a preferred embodiment of the present invention, it is furthermore provided that the medical implant, for separating the two components, includes at least one heating element, which is configured to melt the thermoplastic material of the seal. According to one embodiment, it is provided that the heating element is configured as a heating conductor, which is configured to melt the thermoplastic material of the seal when a predefined electrical current flows through the heating conductor. For this purpose, the heating conductor includes, for example, two electrical contacts, which can be connected to a voltage source. According to an alternative embodiment, it is provided that the heating element is configured to melt the thermoplastic material of the seal when the heating element is exposed to a magnetic field, in particular an alternating magnetic field, or high frequency radio waves.

According to one embodiment of the invention, it is furthermore provided that the at least one heating element, and in particular the heating conductor, is embedded into the seal or disposed on one of the surfaces of the components.

According to one embodiment, it is furthermore provided that the at least one heating element, and in particular the heating conductor, is disposed on the first component or on the second component.

According to one embodiment, it is furthermore provided that the implant includes a further heating element, and in particular a heating conductor, wherein in particular the at least one heating element is disposed on the first component, and wherein the further heating element is disposed on the second component or in the seal.

The further heating element is likewise preferably embedded into the seal or disposed on the surface of the second component.

The two components can then be separated from one another by either using the one heating element, or the further heating element, or both heating elements, to melt the seal and/or an adjoining region of the respective surface (for example, Joule heating as a result of the current in a particular heating conductor).

According to one embodiment of the invention, it is furthermore provided that the seal includes an elastically deformable sealing element, which is preloaded with respect to the two components or surfaces.

According to one embodiment of the Invention, it is preferably provided in this regard that the seal includes an inner and an outer material region, wherein the two material regions are each formed of a thermoplastic material, and wherein the sealing element is disposed between the two material regions.

As a result of the preloading of the elastically deformable or deformed sealing element, this sealing element pushes the two components apart when the seal is being melted or the two material regions are being melted (for example, by one of the heating elements or by externally generated heat).

According to a further embodiment of the invention, it is provided that at least one preloaded spring element is embedded into the seal so that the two components are pushed away from one another by the at least one spring element when the seal is being melted.

According to a preferred embodiment of the invention, it is furthermore provided that the first component is formed by a first flat cable. According to another embodiment, it is provided that the second component is formed by a second flat cable. Such a flat cable is, in particular, characterized in that a lead body of the flat cable has a width that is greater than a height of the flat cable perpendicular to the width.

In particular, according to one embodiment of the invention, the plurality of the contacts of the second component can be disposed on the aforementioned surface of the second component (for example, when the two components are formed by flat cables).

According to an alternative preferred embodiment, it is provided that the first component is formed by a flat cable, and that the second component is formed by an implantable medical device, wherein the contacts of the second component are contacts of a feedthrough of the medical device. A plurality of electrical conductors of the device is guided out of a housing of the device via the feedthrough of the medical device. The medical device can be a pulse generator for neurostimulation, a cardiac pacemaker, or a cardioverter-defibrillator, for example.

The electric conductors of the device are, in particular, embedded into an insulator (for example, a ceramic insulator) of the feedthrough, so that, in particular, the aforementioned contacts of the second component are exposed and/or protrude from the insulator.

In the case of a feedthrough, it is provided according to one embodiment of the invention that the aforementioned surface of the second component extends around the contacts of the second component. The seal to be formed between the two surfaces of the components can thus, in turn, seal the contacts of the components that contact one another.

With the objects of the invention in view, there is also provided a method for producing a medical implant, comprising the following steps:

providing a first component and a second component of the medical implant, wherein the first component includes a surface and a plurality of electrical contacts, the plurality of electrical contacts are in particular disposed on the surface, the second component includes a surface and a plurality of electrical contacts, and the surfaces are formed of a thermoplastic material; and pushing the two components against one another, and melting a seal that is made of the thermoplastic material and is disposed between the two surfaces, so that the seal bonds with the two surfaces, and so that each contact of the first component contacts an assigned contact of the second component in an electrically conducting manner.

After the seal has cured, the two components are preferably fixedly joined to one another.

According to one embodiment of the method, it is provided that the seal (at least before the aforementioned melting) includes two material regions formed of the thermoplastic material.

According to one embodiment of the method, it is furthermore provided that the material regions are secured or fixed on the surface of the first component or on the surface of the second component prior to being melted.

According to one embodiment of the method, it is furthermore provided that an elastically deformable sealing element is disposed between the two material regions, wherein the sealing element can bear against the two surfaces as the two components are being pushed against one another (and as the seal is being melted), and can be preloaded with respect to the two surfaces. The aforementioned sealing element can, for example, be made of a silicone (see also above). According to one embodiment of the method, it is furthermore provided that the sealing element has an annular or circumferential configuration and laterally surrounds or extends around the contacts.

According to a further embodiment of the method, it is provided that the one material region, prior to being melted, is secured on the surface of the first component, wherein the other material region, prior to being melted, is secured on the surface of the second component.

According to one embodiment of the method, it is furthermore provided that, as the seal is being melted, at least one spring element is embedded into the seal, and is preloaded with respect to the components when these are pushed against one another.

The sealing element or the two material regions can be melted by externally generated heat in the event that neither of the two components includes a heating conductor.

According to one embodiment of the method, it is furthermore provided that the seal (in particular the two material regions) is melted by using a heating element that is disposed on the first component, and/or that the seal (in particular the two material regions) is melted by using a heating element that is disposed on the second component. The heating element can include an internal energy source (battery for a heating conductor) or be supplied by an external energy source. The external energy source can supply the heating element, and in particular a heating conductor, with electrical energy in the process. As an alternative, however, it is also possible to introduce energy via a magnetic field, and in particular an alternating magnetic field, or by way of an RF coupler (high frequency radio waves).

According to one embodiment of the method, the heating element of the first component can be embedded into the seal or be disposed on the surface of the first component.

According to one embodiment of the method, it is furthermore provided that the heating element of the second component is embedded into the seal or disposed on one of the surfaces of the second component.

According to one embodiment of the method, it is furthermore provided that the two components are pushed against one another by a tool, which includes a screw-in piston for exerting a force on the two components.

The tool can furthermore include a spring element, in particular in the form of a leaf spring ring or a diaphragm spring, wherein the spring element is disposed between the piston and the first or second component, so that the force generatable by the piston can be introduced via the spring element of the tool into the first or second component.

According to one embodiment of the method, it is furthermore provided that the first component is formed by a first flat cable. According to one embodiment of the method, it is furthermore provided that the second component is also formed by a (second) flat cable.

According to one embodiment of the method, it is furthermore provided (see above) that the plurality of the contacts of the second component are disposed on the aforementioned surface of the second component (for example when the two components are formed by flat cables).

According to an alternative embodiment of the method, it is provided that the first component is formed by a flat cable, and that the second component is formed by an implantable medical device, wherein the contacts of the second component are contacts of a feedthrough of the medical device (see also above).

In the case of a feedthrough, it is provided according to one embodiment of the method that the aforementioned surface of the second component extends around the contacts of the second component. The seal to be formed between the two surfaces of the components can thus, in turn, seal the contacts of the components that contact one another.

The medical device can be a pulse generator for neurostimulation, a cardiac pacemaker, or a cardioverter-defibrillator, for example.

According to one variant of the method, it is furthermore provided that the seal, for separating the two components from one another, is melted again by the action of heat, wherein the heat is generated in one of the following ways: by an external heat source, by the heating element of the first component and/or by the heating element of the second component.

Other features which are considered as characteristic for the invention are set forth in the appended claims.

Although the invention is illustrated and described herein as embodied in a medical implant and a method for producing such an implant, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL VIEWS OF THE DRAWING

FIG. 9 shows a top view onto a first component (flat cable) of a further embodiment of a medical implant according to the invention, including a thermoplastic seal, which includes an additional elastically deformable sealing element (for example, made of silicone), wherein the first component furthermore includes a heating conductor for melting the seal;

FIG. 10 shows a cross-sectional view of the flat cable shown in FIG. 9;

FIG. 15 shows a sectional view of the implant of FIG. 14 removed from the tool;

FIG. 16 shows a top view onto a first component (flat cable) of a further embodiment of a medical implant according to the invention, including a thermoplastic seal, and a heating conductor for melting the seal;

FIG. 17 shows a sectional view of the first component or of the first flat cable according to FIG. 16, which is joined to a second flat cable of the implant by way of the seal fused to the surfaces of the flat cables;

DETAILED DESCRIPTION OF THE INVENTION

Figure 1:
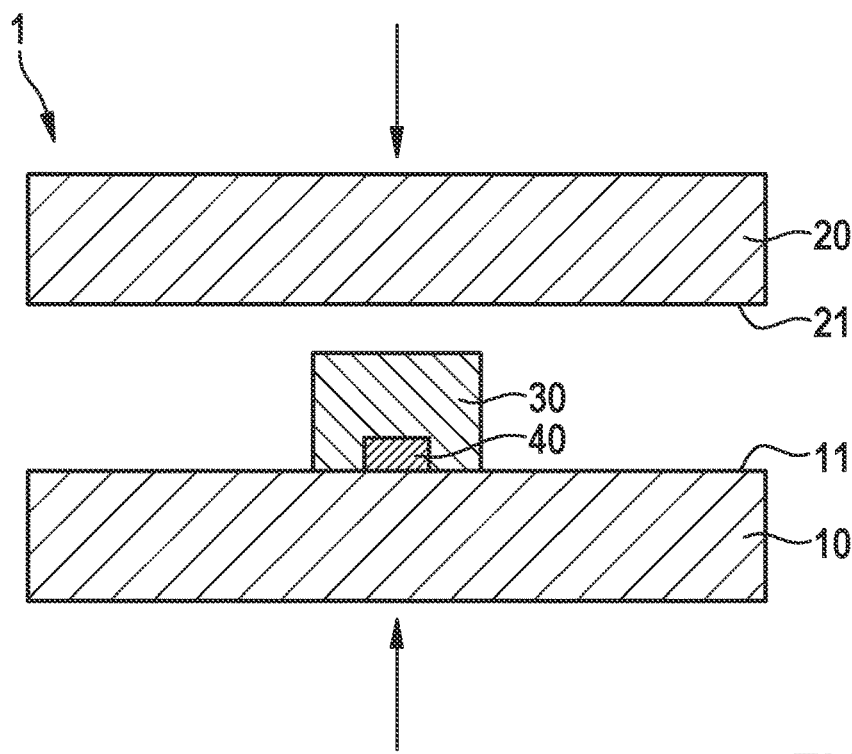
FIG. 1 shows a diagrammatic, cross-sectional view of one embodiment of the invention, wherein the seal and the heating conductor are initially secured on the same surface of one component of the implant.

Referring now to the figures of the drawings in detail and first, particularly, to FIGS. 1 to 4 thereof, there is seen a diagrammatic illustration of the principle of producing sealing between two components 10, 20 of a medical implant 1. The medical implant includes a first component 10 and a second component 20, which can be flat cables 10, 20, for example. One of the two components can also be formed by an implantable medical device 20, for example in the form of a pulse generator (see below). Each of the two components 10, 20 includes a surface 11, 21, on which respective contacts 12, 22 are disposed (for example in the form of contact arrays), wherein the contacts 12 of the first component 10 are connected to the contacts 22 of the second component 20 in an electrically conducting manner, and more particularly by way of mechanical contact. The contacts 12, 22 on both sides preferably include a gold metallization for this purpose. So as to now ensure reliable sealing of these contacts 12, 22, which is necessary in the case of implants 1, the implant 1 according to the invention includes a seal 30, which extends along the surfaces 11, 21 around the contacts 12, 22 that are in contact with one another. For the sake of clarity, the positions of the contacts 12, 22 are not shown in FIGS. 1 to 4 but can be derived from the embodiments described with regard to FIGS. 5 to 24.

According to the invention, it is provided that the seal 30 and the two surfaces 11, 21 are formed of a thermoplastic material (see above, for example), wherein the seal 30 is fused to the two surfaces 11, 21 for sealing the contacts 12, 22 and can be melted so as to separate the two components 10, 20 from one another. This means that the components fixedly joined to one another by way of the seal 30 can be separated from one another again, if needed, by melting the seal 30.

As is diagrammatically apparent based on FIG. 1, the seal 30 or a corresponding material region made of a thermoplastic material can already be present directly on one of the interfaces or surfaces, which here is the surface of the first component 10. The heating conductor 40 can also be disposed on the surface 11 or can be embedded into the seal 30. In this way, the heat of the heating conductor can penetrate the thermoplastic resin well.

Figure 2:
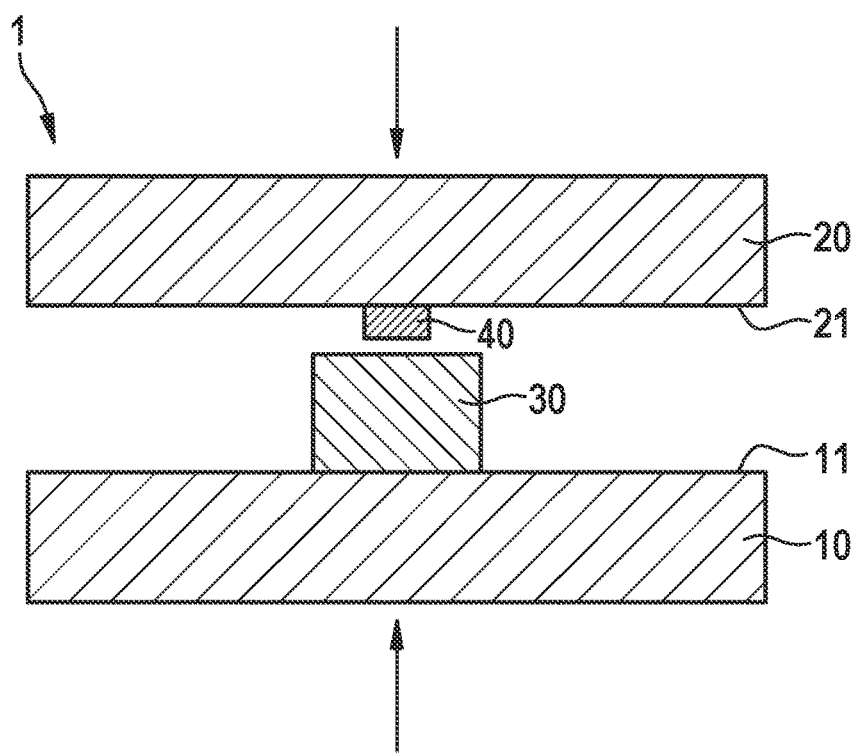
FIG. 2 shows a diagrammatic, cross-sectional view of one embodiment of the invention, wherein the seal and the heating conductor are initially secured on surfaces of different components of the implant.

According to FIG. 2, as an alternative, the heating conductor 40 can be disposed on the one interface or surface 21, while the seal/material region 30 to be melted is disposed on the opposite interface or surface 11.

Figure 3:
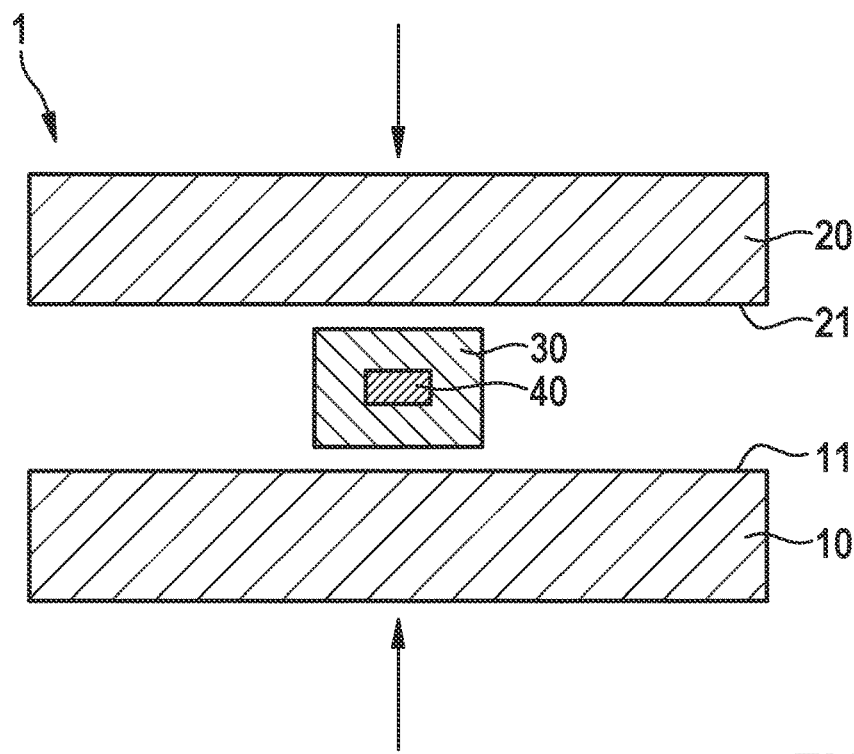
FIG. 3 shows a diagrammatic, cross-sectional view of one embodiment of the invention, wherein the heating conductor is integrated or embedded into the seal.

According to FIG. 3, the seal 30 can initially also form a separate component, wherein the heating conductor 40 can be embedded into the seal 30 here. In this variant, the seal is thus independent, to a certain degree, of the interfaces or surfaces 11, 21.

Figure 4:
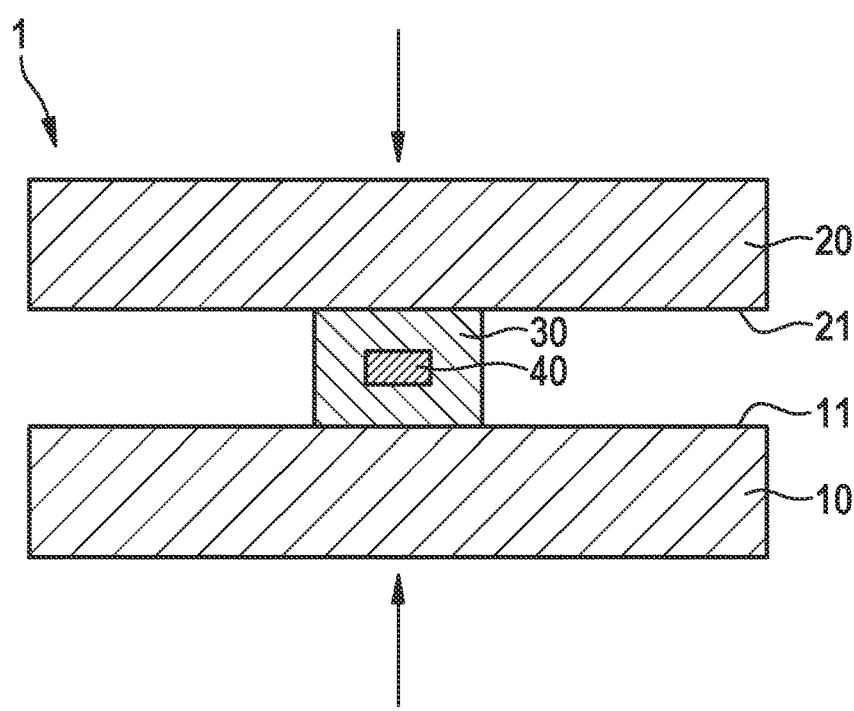
FIG. 4 shows a diagrammatic, cross-sectional view of the fusing of the seal according to FIG. 3 to the surfaces of the two components of the implant.

FIG. 4 shows a diagrammatic manner of the melting of the seal 30 by the heating conductor 40. When the thermoplastic seal 30 is melted in conjunction with the thermoplastic interfaces or surfaces 11, 21, the interfaces disappear, that is, the seal 30 bonds with the surfaces 11, 21. In this way, enhanced sealing can be achieved. As a result, it is possible to seal an entire electrode array 12, 22 with respect to the surrounding area using a single seal 30.

As is shown in FIGS. 1 to 4, the seal 30 can be melted by a heating conductor 40. However, it is also possible to melt the seal 30 using externally generated heat. A corresponding embodiment of the invention is shown in FIGS. 5 to 8. According to this embodiment, the medical implant 1 includes two components 10, 20 in the form of flat cables 10, 20, having contacts 12, 22 that are to be connected to one another in an electrically conducting manner, while also sealing the contacts 12, 22 by the thermally activatable seal 30.

Figure 5:
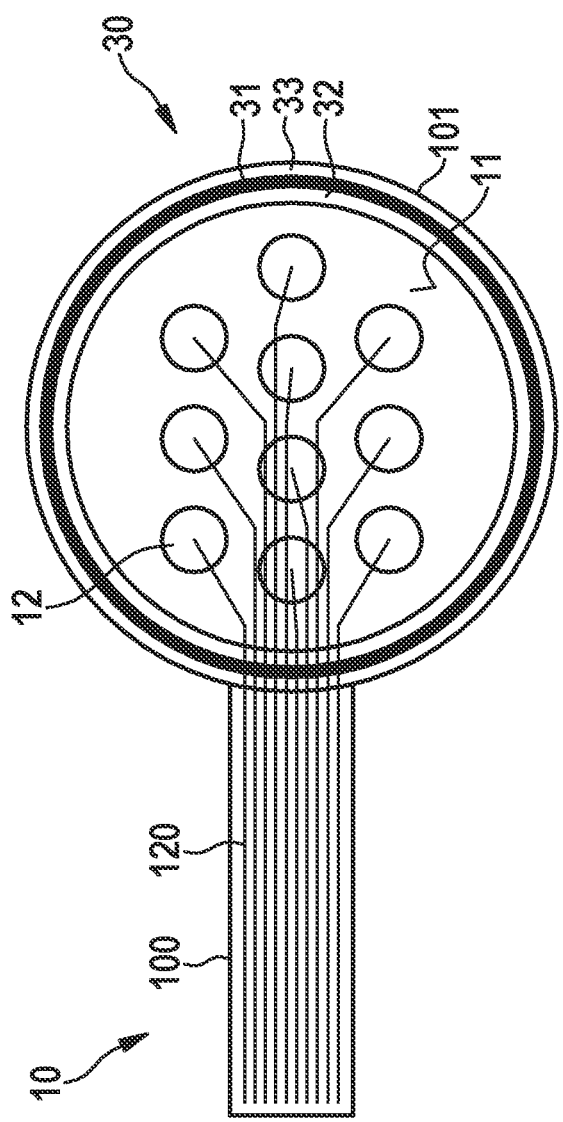
FIG. 5 shows a top view onto a first component (flat cable) of one embodiment of a medical implant according to the invention, including a thermoplastic seal, which includes an additional elastically deformable sealing element (for example, made of silicone)
Figure 6:
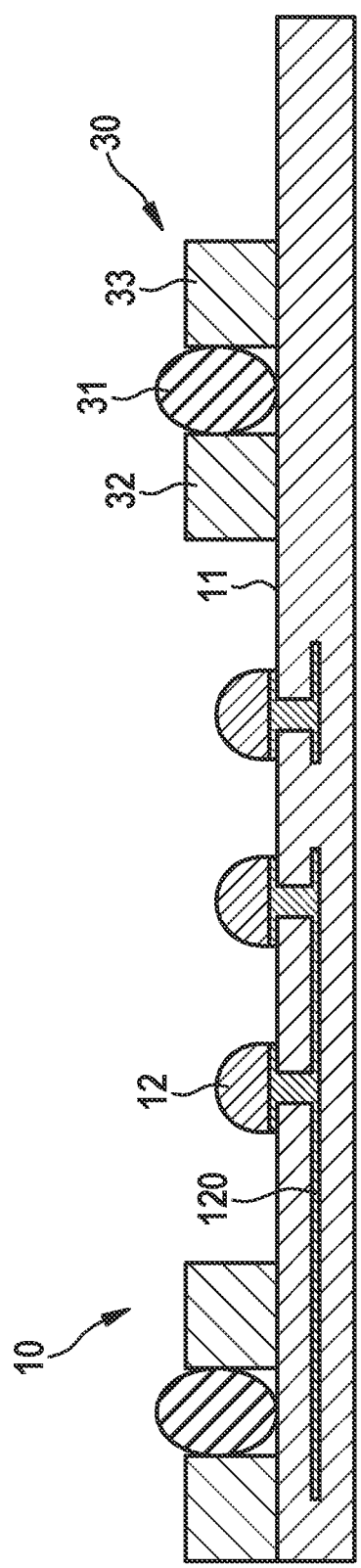
FIG. 6 shows a cross-sectional view of the flat cable shown in FIG. 5.

The first flat cable 10 is shown in FIGS. 5 and 6 and includes a lead body 100, which surrounds the individual electrical conductors 120 of the flat cable 10. The first flat cable 10 furthermore includes a circular end section 101, for example, including a surface 11 on which a plurality of contacts 12 are disposed, which preferably include a gold metallization. Each contact 12 is connected to one of the conductors 120.

Figure 7:
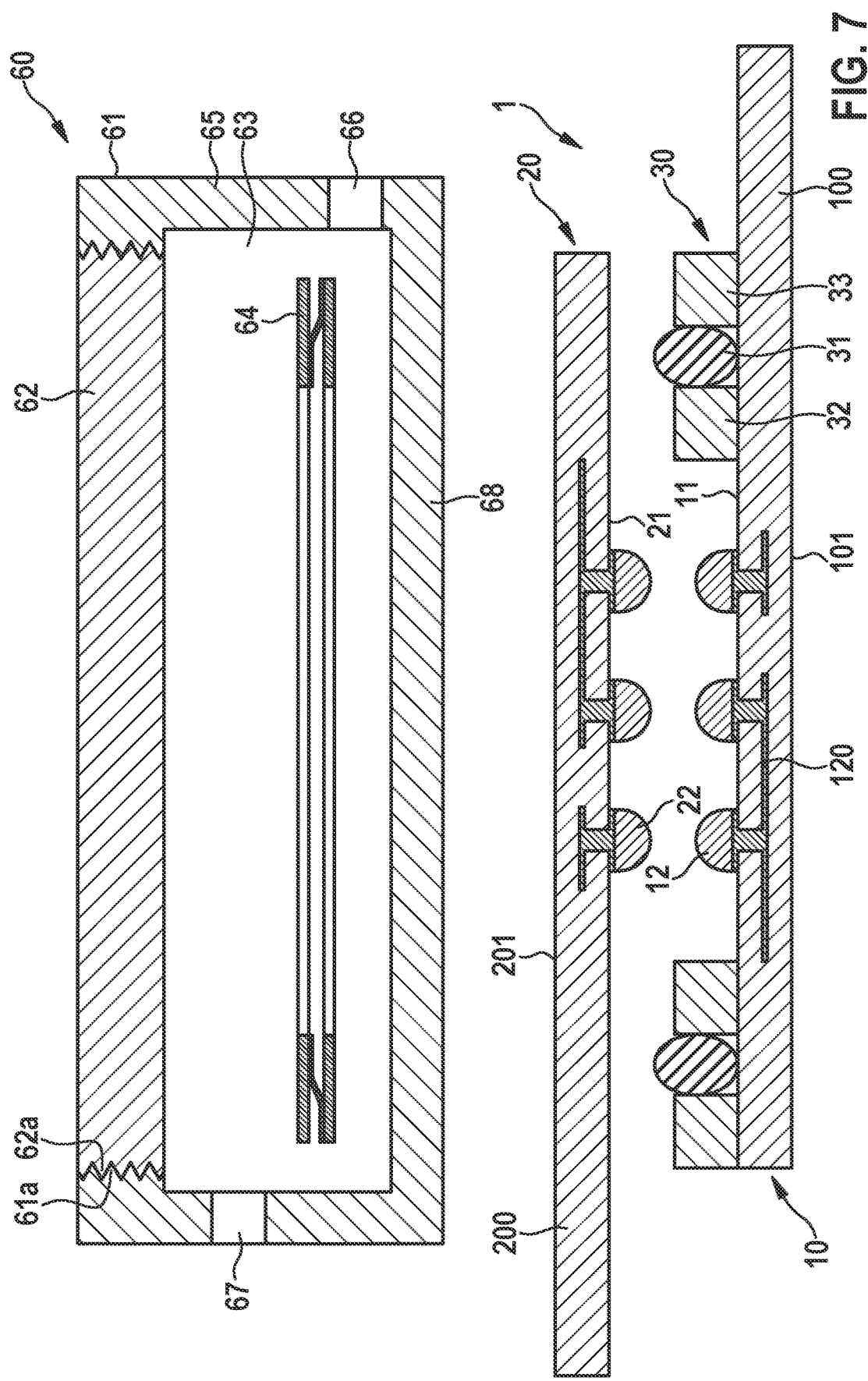
FIG. 7 shows, in addition to the first component of FIGS. 5 and 6, a sectional view of a second component in the form of a second flat cable, and a tool for pushing the two components or flat cables against one another as the seal is being melted.
Figure 8:
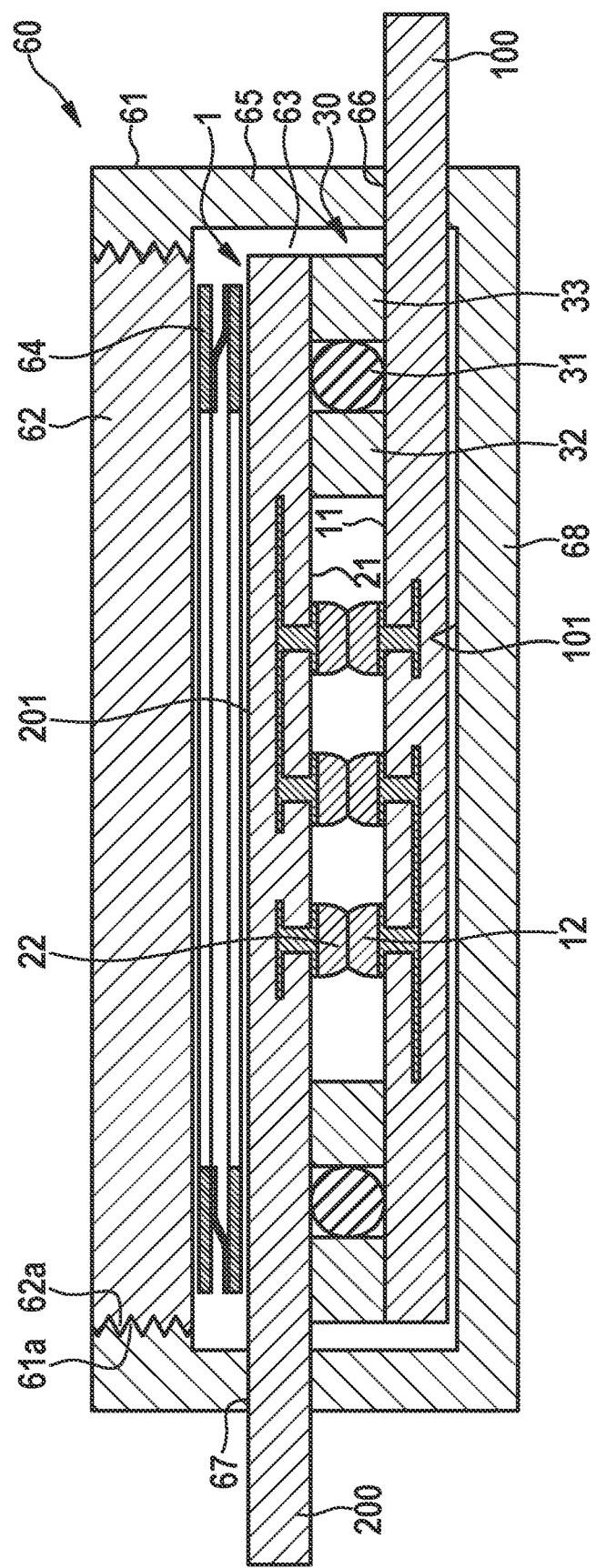
FIG. 8 shows a sectional view of the two flat cables disposed in the tool according to FIGS. 5 to 7 after the seal has been fused to the surfaces of the flat cables for sealing the contacts of the flat cables.
Figure 11:
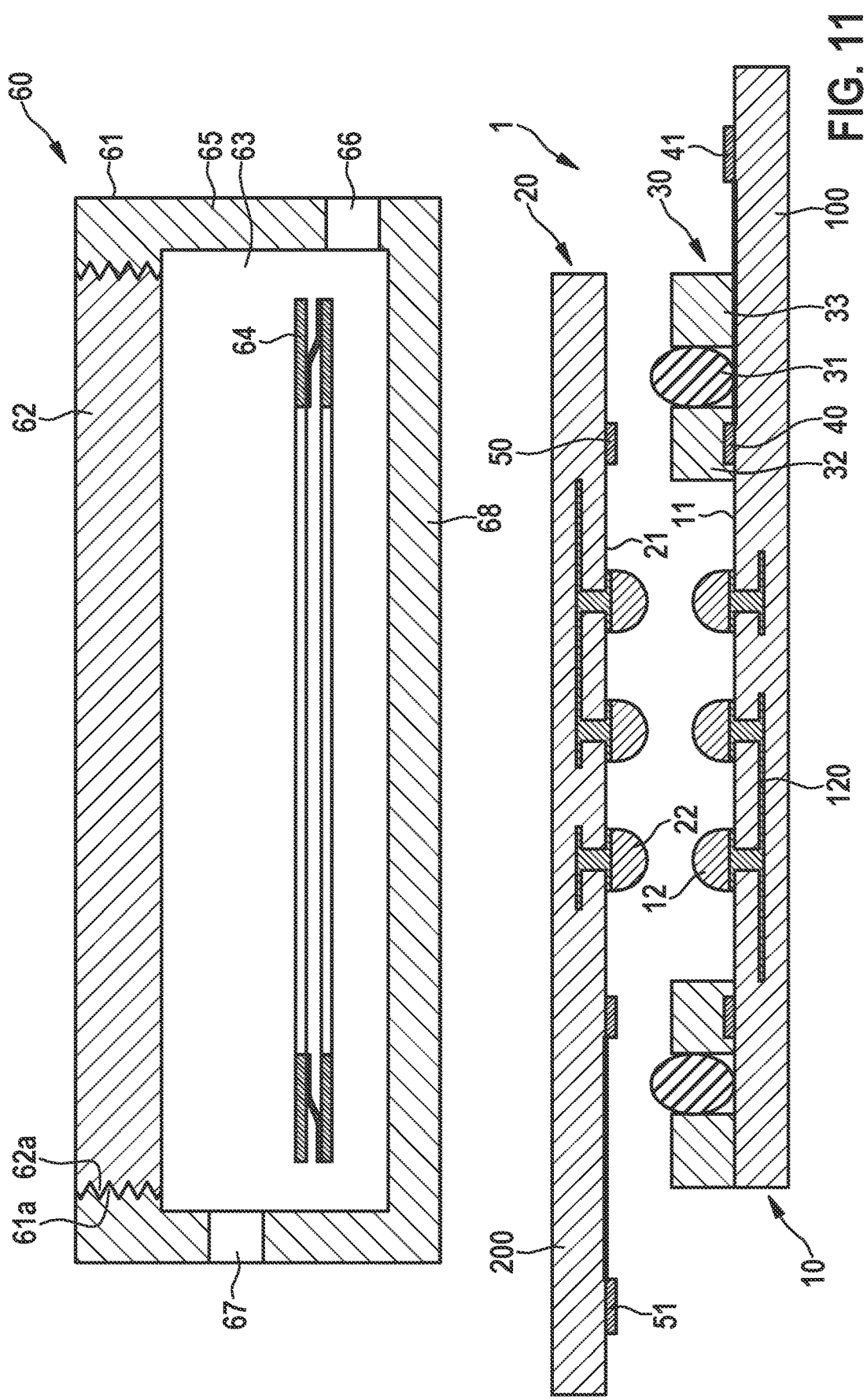
FIG. 11 shows, in addition to the first component of FIGS. 9 and 10, a sectional view of a second component in the form of a second flat cable including a heating conductor, and a tool for pushing the two components or flat cables against one another as the seal is being melted.
Figure 12:
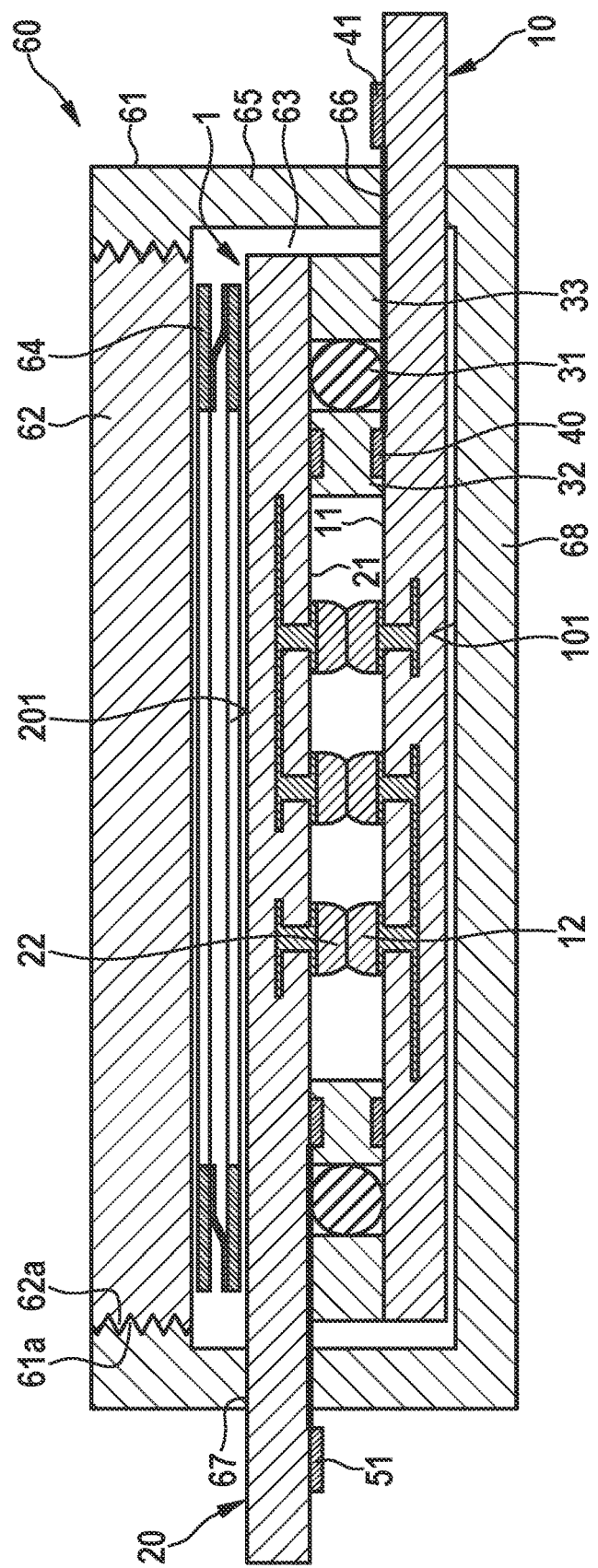
FIG. 12 shows a sectional view of the two flat cables disposed in the tool according to FIGS. 9 to 11 after the seal has been fused to the surfaces of the flat cables for sealing the contacts of the flat cables.

According to FIG. 5, the contacts 12 are surrounded by a seal 30 before the first flat cable 10 is joined to the second flat cable 20 (see FIG. 7). According to FIGS. 5 to 7, this thermoplastic seal 30 includes two material regions 32, 33 made of a thermoplastic material, namely a circumferential or annular inner material region 32 and a circumferential or annular outer material region 33, wherein a groove is present between the two material regions 32, 33, in which an elastically deformable sealing element 31 (such as an O-ring made of silicone) is disposed. The material regions 32, 33 protrude from the surface 11 of the first flat cable 10, which is likewise formed of the thermoplastic material.

The two flat cables 10, 20 are now placed on top of one another, so as to be joined or so as to produce the implant 1 according to FIG. 7, and are pushed against one another using a tool 60, wherein furthermore the seal 30 is melted (for example by supplying external heart), so that the two material regions 32, 33 of the seal 30 bond with the two thermoplastic surfaces 11, 21 of the flat cables 10, 20. According to FIG. 8, the sealing element 31 is embedded into the seal 30 in the process, and is preloaded with respect to the two components 10, 20 of the implant 1. During a later melting of the seal 30, the sealing element 31 then pushes the two components apart for improved separation.

So as to push the two components 10, 20 or flat cables 10, 20 of the plant 1 against one another, the tool 60 includes a housing 61 having an internal thread 61a, in which an external thread 62a of an accordingly screw-on piston 62 engages. The housing 61 includes a lateral wall 65 and a bottom 68 that is located opposite the piston 62 and connected to the wall 65. Furthermore, the wall 65 includes cut-outs 66, 67 through which portions of the flat cables 10, 20 (such as sections of the respective lead body 100, 200) can be guided out of an interior 63 of the tool 60 or housing 61. The interior 63 thus preferably only accommodates the end sections 101, 201 of the flat cables 10, 20 which are located on top of one another. The two flat cables 10, 20 or end sections 101, 201 are disposed between the piston 62 and the bottom 68 in the process. Moreover, a spring element 64, in particular in the form of a leaf spring ring or a diaphragm spring, is preferably disposed between the piston 62 and the upper second flat cable 20. When the piston 62 is now screwed into the housing 61, the piston 62, by way of the spring element 64, pushes against the second flat cable 20, which, in turn, pushes against the first flat cable 10 by way of the seal 30. Melting of the seal 30 or of the thermoplastic material regions 32, 33 causes these to bond with the surfaces 11, 21, and the contacts 12, 22 of the flat cables 10, 20 located opposite one another end up on top of one another so as to be in electrically conducting contact.

FIGS. 9 to 12 show a modification of the embodiment shown in FIGS. 5 to 8, wherein here, in contrast to FIGS. 5 to 8, a respective heating conductor 40 or 50 is integrated into the first flat cable 10 and into the second flat cable 20. The heating conductor 40 of the first flat cable 10 is disposed beneath the seal 30 to be melted, whereas the heating conductor 50 of the second flat cable 20 is disposed on the surface 21 and later, after the two flat cables 10, 20 have been joined, is likewise hidden by the seal 30. After the seal 30 has been fused to the surfaces 11, 21, each of the two heating conductors 40, 50 can thus be used to re-melt the cured seal 30.

So as to be able to supply the heating conductors 40, 50 with power, while the end sections 101, 201 of the flat cables 10, 20 are disposed in the interior 63 of the tool 60, the contacts 41, 51 of the heating conductors 40, 50 are guided out of the tool 60, for example through the cut-outs 66 and 67 of the housing 61.

Moreover, the embodiment shown in FIGS. 9 to 12 can be further simplified by dispensing with the sealing element 31. In this case, the seal 30 is formed by a single material region to be fused to the surfaces 11, 21, according to FIGS. 16 and 17.

Figure 13:
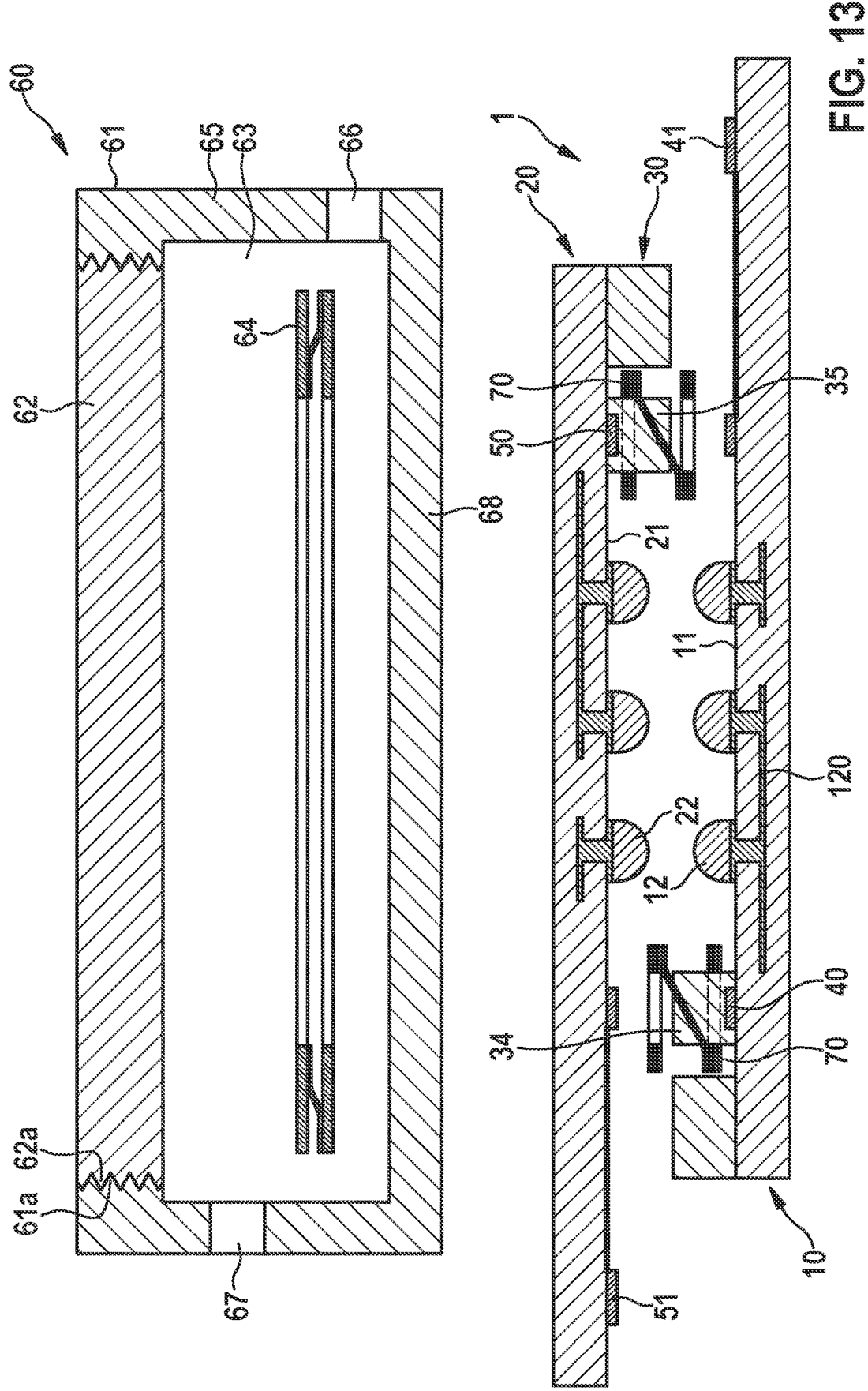
FIG. 13 shows a sectional view of a further embodiment of a medical implant according to the invention, including a first and a second component in the form of a flat cable, wherein a material region and a spring element of the seal to be produced are secured on the particular flat cable, and furthermore shows the tool for pushing the two components or flat cables against one another as the material regions of the seal are being melted.
Figure 14:
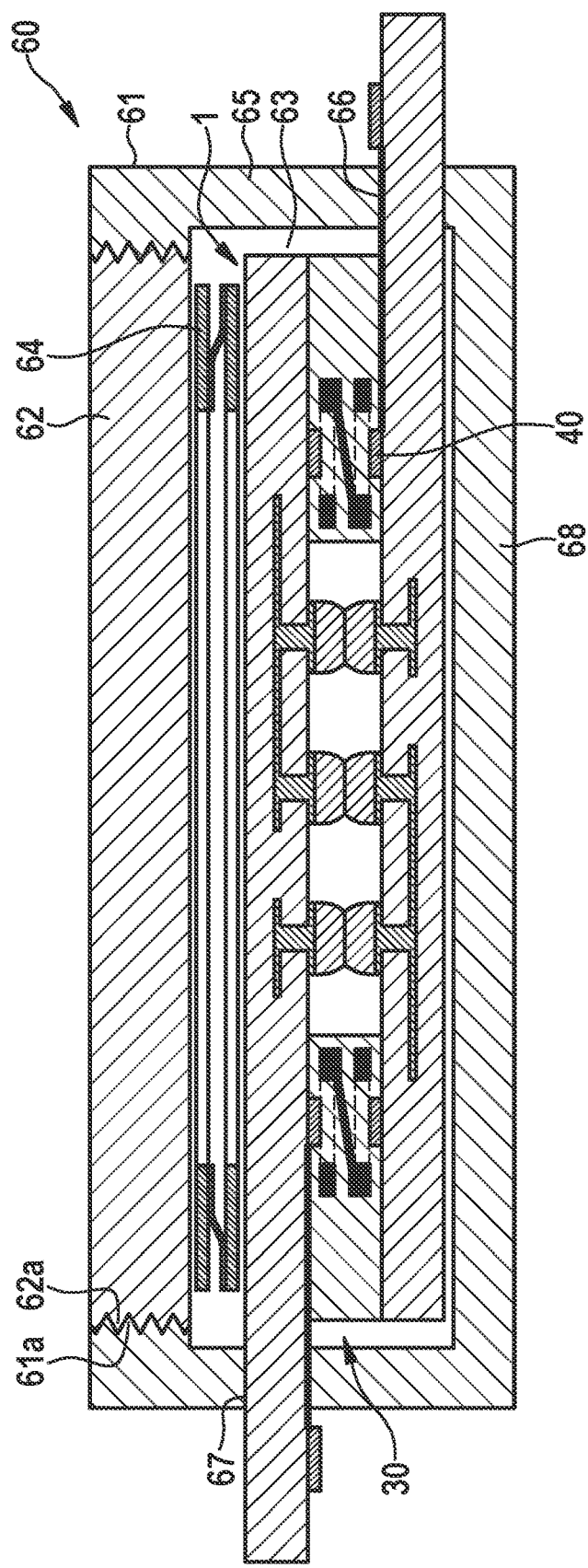
FIG. 14 shows a sectional view of the two flat cables disposed in the tool according to FIG. 13, after the material regions of the seal have been fused to the surfaces of the flat cables for sealing the contacts of the flat cables, wherein the spring elements embedded into the seal are preloaded with respect to the two flat cables.

FIGS. 13 to 15 furthermore show a modification of the embodiment of the implant 1 shown in FIGS. 6 to 12, wherein according to FIGS. 13 to 15 two spring elements 70 are embedded into the seal 30, instead of an elastically deformable spring element 31 in the form of a silicone seal.

For this purpose, the first flat cable 10 includes a material region 34 made of a thermoplastic material, which projects from the surface 11 and on which a spring element 70 is secured. The material region 34 is meltable by a heating conductor 40 disposed beneath the material region 34. Similarly, the second flat cable 20 includes a material region 35 made of the thermoplastic material which protrudes from the surface 21 and on which likewise a spring element 70 is secured. When the two flat cables 10, 20 are now pushed against one another by the tool 60 as described above, and the material regions 34, 35 are melted in the process, the material regions 34, 35 unite with the surfaces 11, 21 and form a circumferential sealing element 30 into which the spring elements 70 can be embedded in the preloaded state. At the same time, the mechanical contact of the contacts 12, 22 is achieved.

Moreover, FIGS. 18 to 24 show embodiments of an implant according to the invention, in which the first component is formed in each case by a flat cable 10, while the second component 20 is an implantable medical device 20 (for example, a pulse generator), which includes a feedthrough 80 by way of which electrical conductors 81, which at the ends thereof form the contacts 22, are guided out of a housing of the device 20. The conductors 81 are, in particular, embedded into an insulator 82 (preferably in the form a ceramic 82) of the feedthrough 80, on which a thermoplastic surface 21 is provided, to which, in turn, the seal 30 can be fused.

Figure 18:
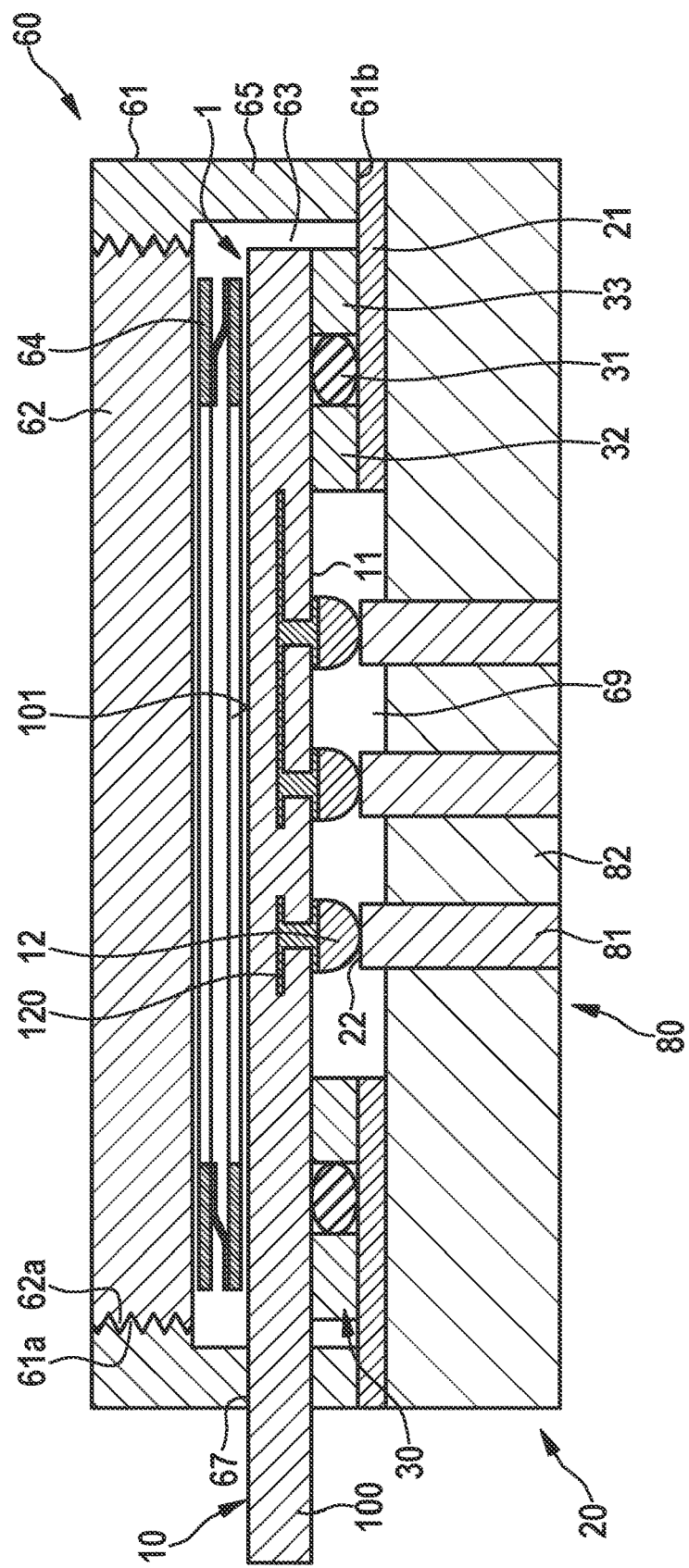
FIG. 18 shows a sectional view of a further embodiment of a medical implant according to the invention, including a first component in the form of a flat cable and a second component in the form of an implantable medical device, wherein the two components are joined to one another by way of a thermoplastic seal meltable by external heat and are disposed in a tool for pushing the two components against one another, wherein the tool is temporarily secured on an outer side of the medical device.

According to FIG. 18, the seal 30, prior to being joined to the device 20, can include two material regions 32, 33 that project from the surface 11 of the flat cable 10 and define a groove into which an elastically deformable sealing element 31 is integrated. The flat cable 10 is now pushed with these material regions 32, 33 against a surface 21 of the device 20 which is likewise made of the thermoplastic material of the material regions 32, 33, wherein the material regions 32, 33 are fused to the surfaces 11, 21 by supplying externally generated heat, so that a sealing joint is established between the flat cable 10 and the implantable medical device 20. Moreover, the sealing element 31 is preloaded with respect to the two components 10, 20 in the process. During a later melting of the seal 30, this facilitates the separation of the two components 10, 20. When the two components 10, 20 of the implant 1 are pushed against one another, the contacts 12 of the flat cable 10 are furthermore mechanically pushed against the contacts 22 of the conductors 81 that are guided out of the device 20 by the feedthrough 80, so that likewise an electrically conductive connection between the contacts 12 of the flat cable 10 and the contacts 22 of the device 20 is established.

FIG. 18 furthermore shows the tool 60, by way of which the end section 101 of the flat cable 10 is pushed, with the seal 30 first, against the thermoplastic surface 21 of the feedthrough 80 of the device 20, while the seal 30 or the material regions 32, 33 thereof are being melted. For this purpose, the tool 60, in turn, includes a housing 61 including a lateral wall 65, wherein, however, the housing 61 no longer includes a bottom 68 (see above), but an opening 69, so that the material regions 32, 33 and the sealing element 31 of the seal 30 can bear against the surface 21 of the device 20. So as to form an abutment for the screw-in piston 62, in the present example an end face 61b of the housing 61 or of the wall 65 delimiting the aforementioned opening 69 is secured on the device 20, for example by a welded joint. As was already described above, the aforementioned piston 62 includes an external thread 62a, which engages in an internal thread 61a of the housing 61 of the tool 60. The piston 62 can thus be caused to carry out a turning motion so as to be movable in a direction toward the end section 101 of the flat cable 10 which is disposed in the interior 63 of the tool housing 61. As before, a spring element 64, which can be a leaf spring ring or a diaphragm spring, for example, is disposed between the piston 62 and the flat cable 10. The piston 62 thus pushes against the flat cable 10 by way of the spring element 64, and pushes the flat cable against the device 20. The seal 30 can be melted in the process, as described above, and the electrical connection between the contacts 12, 22 can be established. Moreover, the wall 65 of the housing can include a cut-out 67, via which, for example, the lead body 100 of the flat cable 10 can be guided out of the housing 61 of the tool 60. After the seal 30 joining the two surfaces 11, 21 has been created by melding of the material regions 32, 33, the tool 60 can be removed again.

Figure 19:
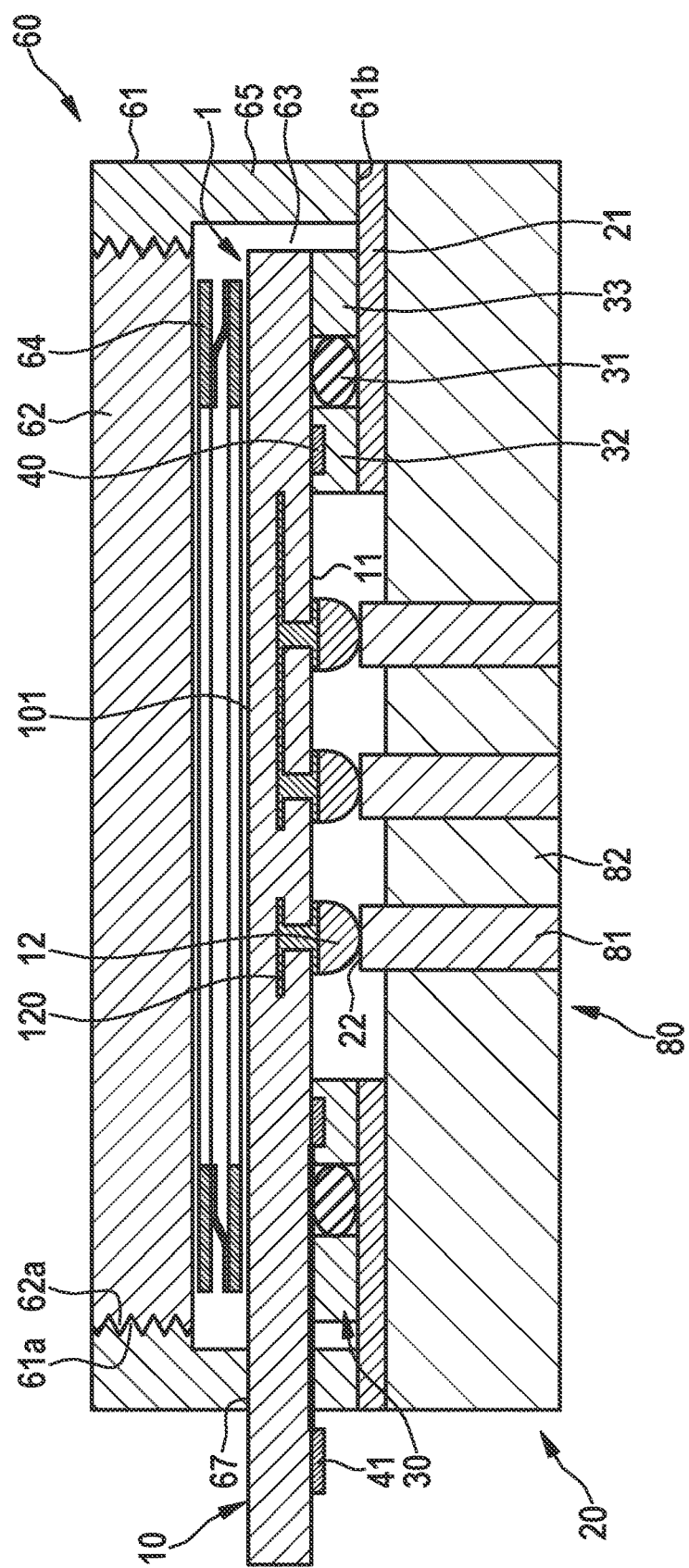
FIG. 19 shows a sectional view of a further embodiment of a medical implant according to the invention, including a first component in the form of a flat cable and a second component in the form of an implantable medical device, wherein the two components are joined to one another by way of a thermoplastic seal meltable by a heating conductor and are disposed in a tool for pushing the two components against one another, wherein the tool is temporarily secured on an outer side of the medical device.
Figure 20:
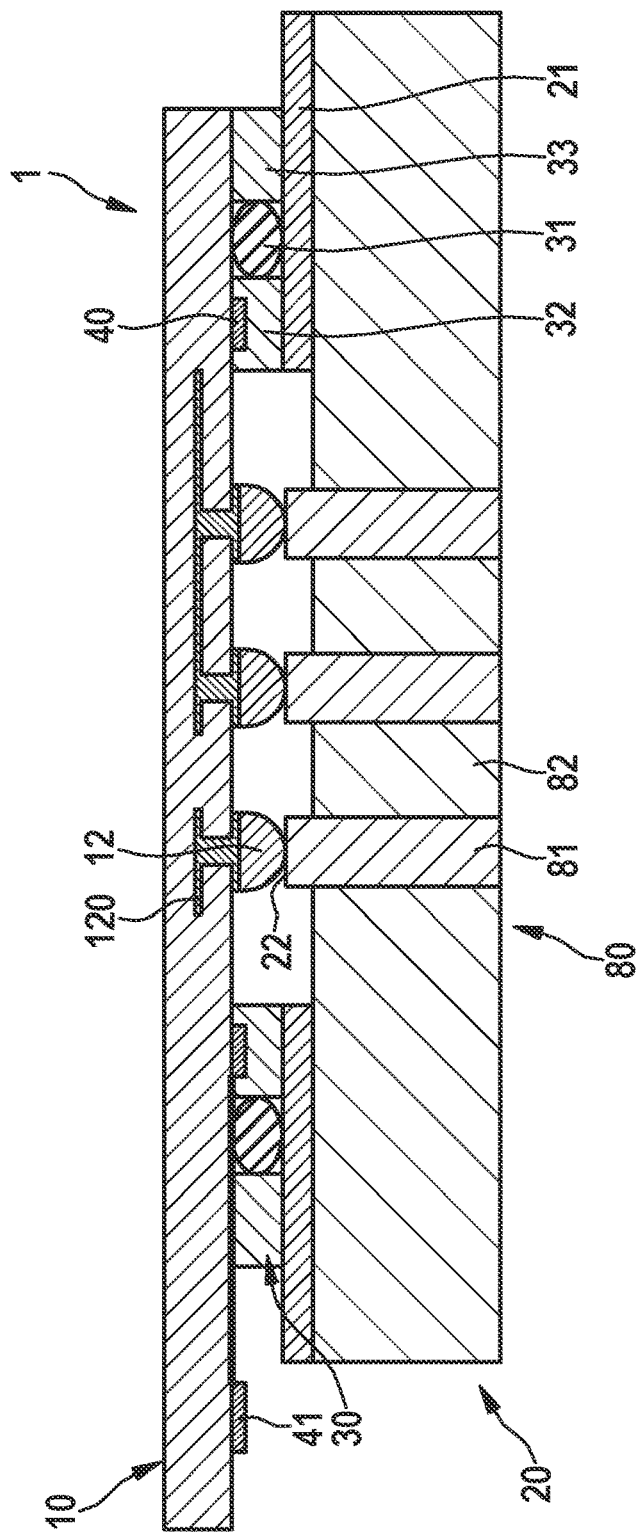
FIG. 20 shows a sectional view of the implant according to FIG. 19 after the tool has been removed.

FIG. 19 shows a modification of the implant 1 shown in FIG. 18, which is formed of the flat cable 10 and the device 20 joined thereto. In this modification, a heating conductor 40 is additionally provided, which is disposed on the surface 11 of the flat cable 10 and, for example, covered by the inner material region 32. Using the heating conductor 40, the seal 30 can now be melted in a targeted manner, so as to bond with the two surfaces 11, 21. Contacts 41 for contacting the heating conductor 40 or for applying a heating voltage to the heating conductor 40 can, for example, be guided out of the tool 60 via a cut-out 67 of the housing 61 or the wall 65 of the tool 60. FIG. 20 shows the implant 1 including the fully formed seal 30 after having been removed from the tool 60.

Figure 24:
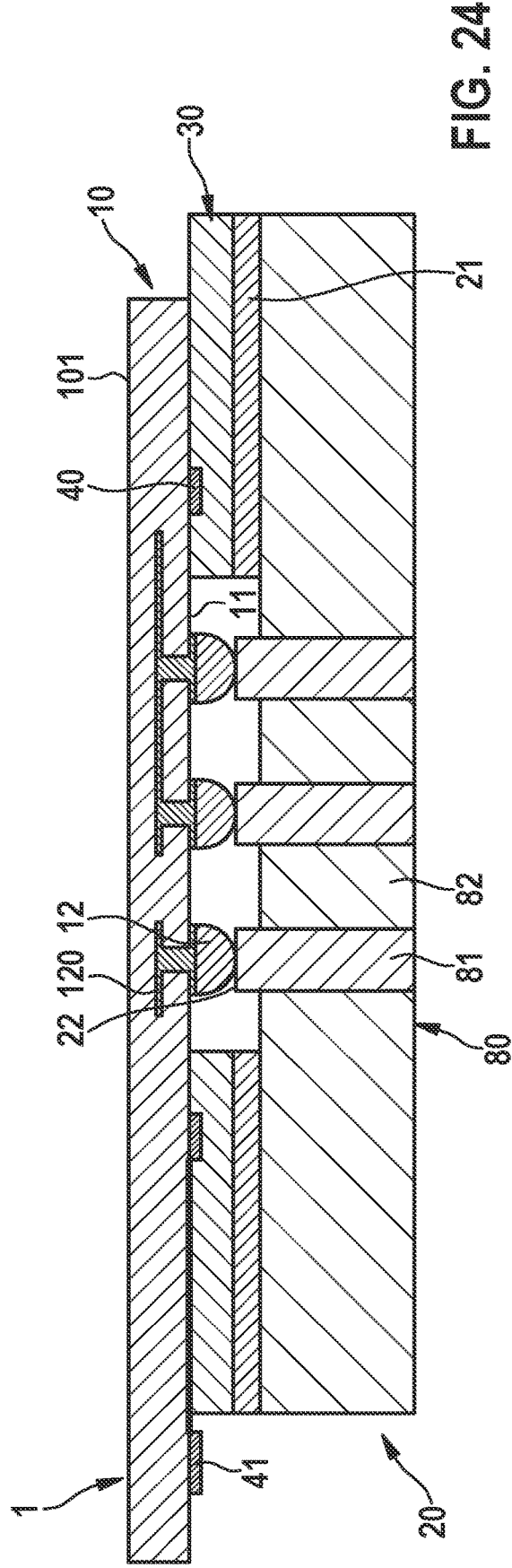
FIG. 24 shows a sectional view of a modification of the implant shown in FIG. 23 after the tool has been removed.

As is apparent from FIG. 24, it is also possible to entirely dispense with the sealing element 31 in the embodiment according to FIG. 19.

Figure 21:
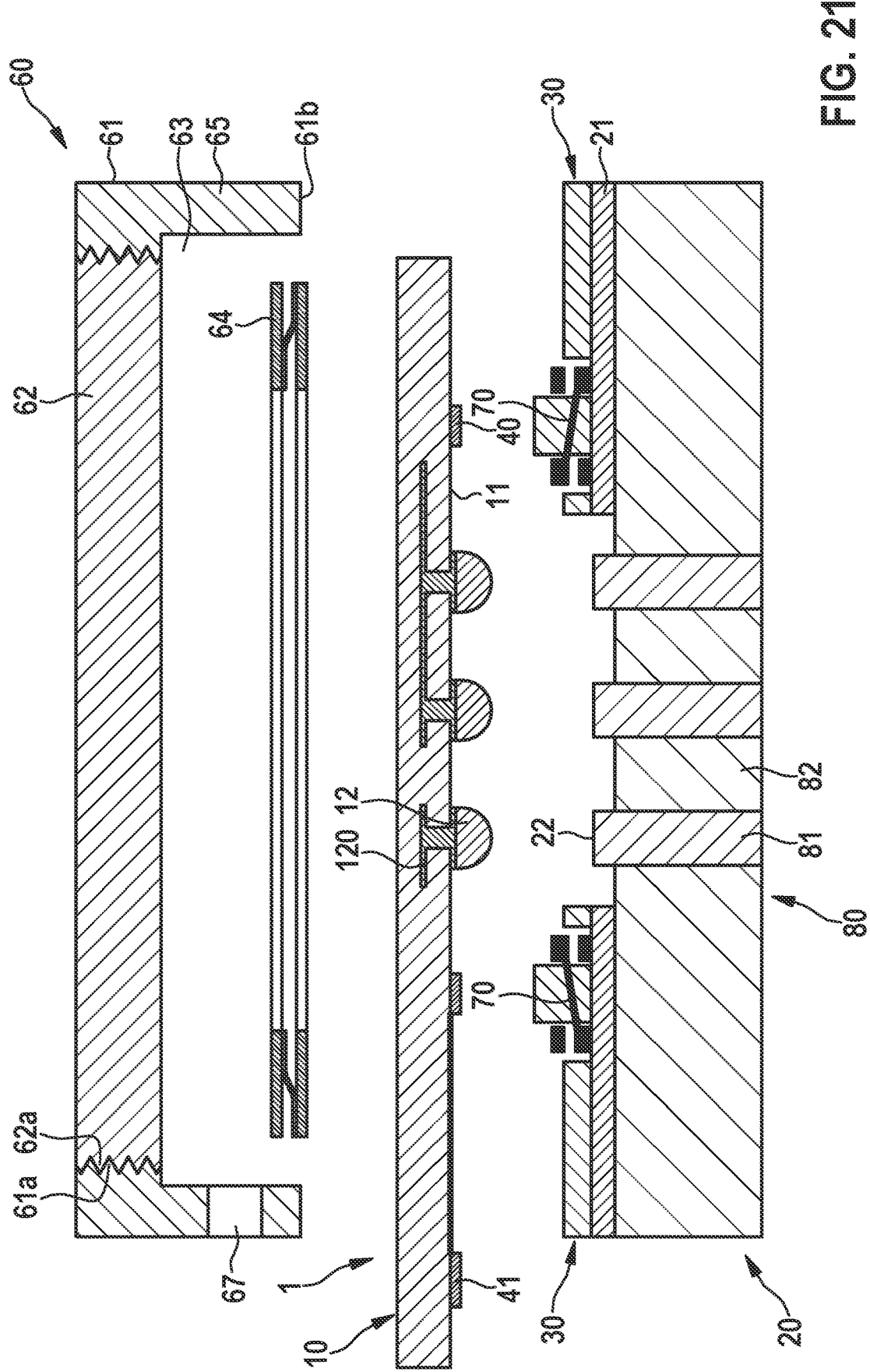
FIG. 21 shows a sectional view of a further embodiment of a medical implant according to the invention, including a first component in the form of a flat cable and a second component in the form of an implantable medical device, wherein a seal, meltable by heating conductors, and a spring element are provided on the device, and furthermore shows the tool for pushing the two components against one another as the seal is being melted.
Figure 22:
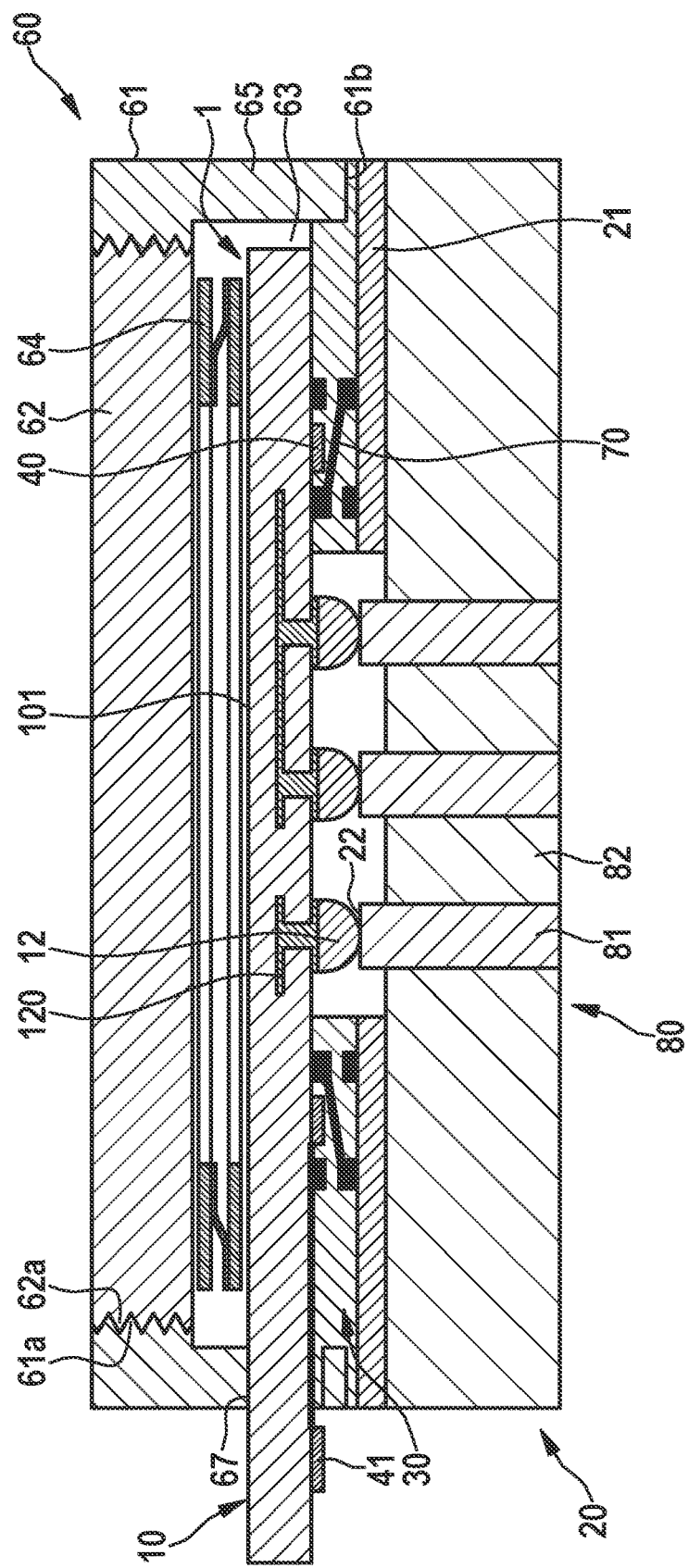
FIG. 22 shows a sectional view of the implant according to FIG. 21 including a formed seal, which is fused to the surfaces of the two components, wherein the tool is secured on the second component in the form of the medical device.
Figure 23:
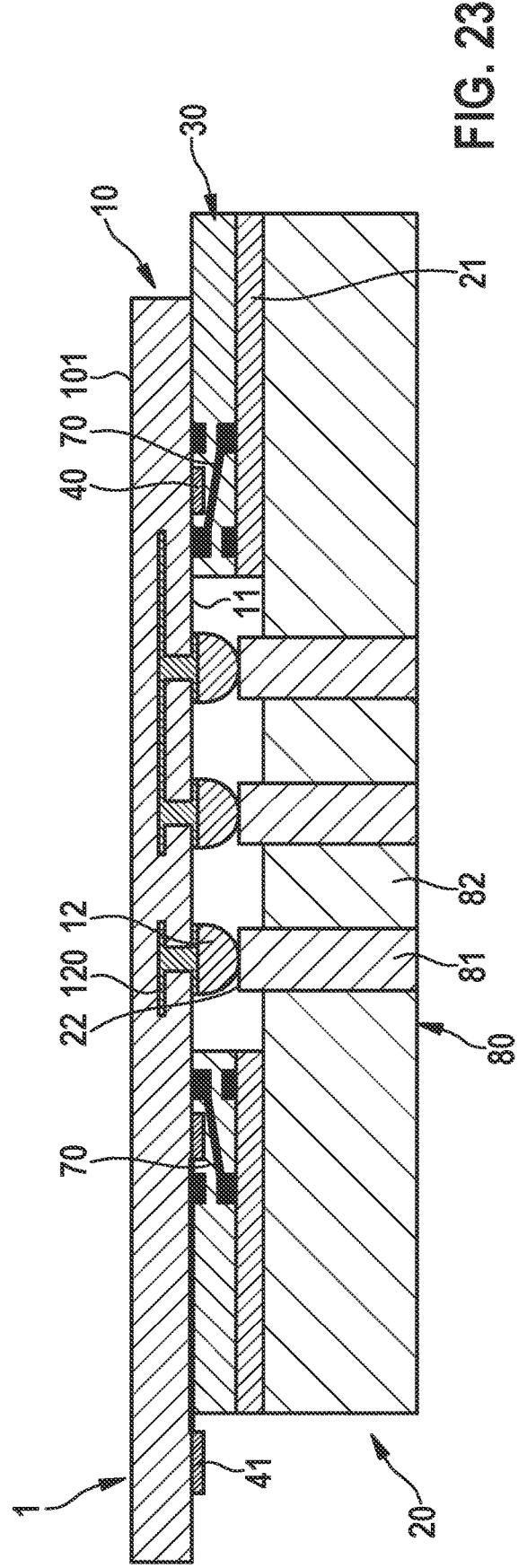
FIG. 23 shows a sectional view of the implant according to FIG. 22 after the tool has been removed.

In combination with FIGS. 22 and 23, FIG. 21 shows a further embodiment of an implant according to the invention, in which a flat cable 10 is joined to the feedthrough 80 of an implantable medical device 20.

Prior to being joined to the flat cable 10, the seal 30 can include a material region 30 which projects from the thermoplastic surface 21 of the device 20 and on which one or more spring elements 70 are disposed. In contrast, a heating conductor 40 is disposed on the opposite thermoplastic surface 11 of the flat cable 10, which is configured to melt the material regions 30 when the flat cable 10 is pushed against the device 20 by the tool 60. The tool 60 can be configured as has been described above in connection with FIG. 18 or 19. FIG. 22 shows the moment at which the seal 30 is produced, which is sealingly fused to the surfaces 11 and 21. In the process, the spring elements 70 are also preloaded with respect to the components 10, 20, which facilitates a later separation of the flat cable 10 and the device 20 when the seal 30 is melted again by the heating conductor 40. FIG. 23 shows the implant 1 after having been removed from the tool 60.

The invention advantageously enables a simplified mechanical configuration of the implant 1, wherein an entire electrode array 12, 22 can be sealed using one seal 30. The invention thus considerably simplifies the configuration of detachable connectors/flat cables for implants, and the costs for the joining technique can be considerably reduced. The seal can advantageously already be located directly on a surface of a component. The heating conductor can be disposed adjoining the same.

The invention claimed is:

1. A medical implant, comprising:
   a first component including a first surface and a plurality of electrical contacts disposed on said first surface;
   a second component including a second surface and a plurality of electrical contacts;
   each of said contacts of said first component electrically conductingly contacting a respective contact of said second component; and
   a seal disposed between said first surface of said first component and said second surface of said second component for sealing said contacts, said first surface being a surface of said first component immediately adjacent to said seal, and said second surface being a surface of said second component immediately adjacent to said seal;
   said seal and said first and second surfaces of said first and second components being formed of a thermoplastic material, said seal being melted to said first and second surfaces of said first and second components for sealing said contacts, and said seal being meltable for separating said first and second components from one another.

2. The medical implant according to claim 1, which further comprises at least one heating element or heating conductor configured to melt said thermoplastic material of said seal for separating said first and second components.

3. The medical implant according to claim 2, wherein said at least one heating element is embedded into said seal or disposed on one of said first or second surfaces.

4. The medical implant according to claim 1, wherein said seal includes an elastically deformable sealing element or spring element, being preloaded relative to said first and second components.

5. The medical implant according to claim 1, wherein said first component is formed by a first flat cable, and said second component is formed by a second flat cable.

6. The medical implant according to claim 1, wherein said first component is formed by a flat cable, said second component is formed by an implantable medical device, and said contacts of said second component are contacts of a feedthrough of said medical device.

7. A method for producing a medical implant, the method comprising:
   providing a first component and a second component of the medical implant, the first component including a first surface and a plurality of electrical contacts disposed on the first surface, the second component including a second surface and a plurality of electrical contacts, and the first and second surfaces being formed of a thermoplastic material; and
   pressing the first and second components against one another, and melting a seal formed of the thermoplastic material and disposed between and immediately adjacent to the first and second surfaces of the first and second components, causing the seal to bond with the first and second surfaces of the first and second components, and causing each contact of the first component to electrically conductingly contact a respective contact of the second component.

8. The method according to claim 7, which further comprises providing the seal with two material regions formed of the thermoplastic material.

9. The method according to claim 8, which further comprises, prior to melting the seal, securing the material regions on the first surface of the first component or on the second surface of the second component.

10. The method according to claim 8, which further comprises placing an elastically deformable sealing element between the two material regions, and preloading the sealing element against the first and second components when the first and second components are pressed against one another.

11. The method according to claim 8, which further comprises, prior to melting the seal, securing one material region on the first surface of the first component and, prior to melting the seal, securing the other material region on the second surface of the second component.

12. The method according to claim 7, which further comprises, during the melting of the seal, at least one spring element is embedded into the seal and is preloaded relative to the components when the first and second components are pressed against one another.

13. The method according to claim 7, which further comprises melting the seal by using at least one of a heating element disposed on the first component or a heating element disposed on the second component.

14. The method according to claim 7, which further comprises using a tool to press the first and second components against one another, and providing the tool with a screw-in piston for exerting a force on the first and second components.

15. The method according to claim 7, which further comprises:
   forming the first component as a first flat cable and forming the second component as a second flat cable, or
   forming the first component as a flat cable and forming the second component as an implantable medical device, and providing the contacts of the second component as contacts of a feedthrough of the medical device.

\* \* \* \* \*